US006245818B1

(12) United States Patent
Lignell

(10) Patent No.: US 6,245,818 B1
(45) Date of Patent: Jun. 12, 2001

(54) MEDICAMENT FOR IMPROVEMENT OF DURATION OF MUSCLE FUNCTION OR TREATMENT OF MUSCLE DISORDERS OR DISEASES

(75) Inventor: Ake Lignell, Varmdo (SE)

(73) Assignee: Astacarotene AB, Gustavsberg (SE)

( * ) Notice: Subject to any disclaimer, the term of this patent is extended or adjusted under 35 U.S.C. 154(b) by 0 days.

(21) Appl. No.: 09/485,704
(22) PCT Filed: Aug. 26, 1998
(86) PCT No.: PCT/SE98/01526
§ 371 Date: Feb. 29, 2000
§ 102(e) Date: Feb. 29, 2000
(87) PCT Pub. No.: WO99/11251
PCT Pub. Date: Mar. 11, 1999

(30) Foreign Application Priority Data

Sep. 4, 1997 (SE) .................................................. 9703191

(51) Int. Cl.⁷ .................................................. A61K 31/12
(52) U.S. Cl. .................................................. 514/691
(58) Field of Search ............................................. 514/691

(56) References Cited

FOREIGN PATENT DOCUMENTS

| WO 8503226 | 8/1985 | (WO) . |
| WO 9500130 | 1/1995 | (WO) . |
| WO 9623489 | 8/1996 | (WO) . |
| 0770385 | 5/1997 | (WO) . |

OTHER PUBLICATIONS

Patent Abstracts of Japan, vol. 14, No. 215, C–716, abstract of JP 2–49091 A, Feb. 19, 1990.
Patent Abstracts of Japan, vol. 18, No. 307, C–1211, abstract of JP 6–65033 A, Mar. 8, 1994.

*Primary Examiner*—Theodore J. Criares
*Assistant Examiner*—Jennifer Kim
(74) *Attorney, Agent, or Firm*—Bacon & Thomas

(57) ABSTRACT

Medicament for the prophylactic and/or therpeutic improvement of the duration of mammalian muscle function and/or treatment of mammalian muscle disorders or diseases, e.g. equine Exertional Rhabdomyolysis, comprising at least one type of xanthophylles, e.g. astaxanthin, is described. Further, the use of xanthophylles in the preparation of such medicaments, and a method of prophylactic and/or therapeutic improvement of the duration of mammalian muscle function and/or treatment of mammalian muscle disorders or diseases, are disclosed.

10 Claims, 3 Drawing Sheets

MEDICAMENT FOR IMPROVEMENT OF DURATION OF MUSCLE FUNCTION OR TREATMENT OF MUSCLE DISORDERS OR DISEASES

The present invention relates to a medicament for the prophylactic and/or therapeutic improvement of the duration of mammalian muscle function and/or treatment of mammalian muscle disorders or diseases, comprising at least one type of xanthophylles, especially astaxanthin. The invention also relates to the use of at least one type of xanthophylles for the production of such a medicament and to a method of prophylactic and/or therapeutic improvement of the duration of mammalian muscle function and/or treatment of mammalian muscle disorders or diseases, e.g. equine Exertional Rhabdomyolysis.

BACKGROUND OF THE INVENTION

Exertional rhabdomyolysis, also referred to as exertional myopathy, tying-up syndrome, azoturia, or Monday morning disease, is probably the most common muscle disorder in horses. Predisposing or associated factors that have been implicated in the pathogenesis of this condition include electrolyte imbalances, hypothyroidism, and vitamin E-selenium deficiency. Therefore, treatment of horses affected by exertional rhabdomyolysis have included pain relief, rehydration and correction of electrolyte abnormalities (See e.g. The Horse: Diseases and Clinical Management, edited by C. N. Kolbluk, T. R. Ames, R. J. Geor, W. B. Saunders Company, Philadelphia, 1995, pp. 809–810).

Xanthophylles, including astaxanthin, is a large group of carotenoids containing oxygen in the molecule in addition to carbon and hydrogen. The carotenoids are produced de novo by plants, fungi and some bacteria. Astaxanthin, in the form of naturally produced algal meal of cultured Haematococcus sp., has been marketed as antioxidant for mammals, especially humans.

DESCRIPTION OF THE INVENTION

The present invention provides a medicament for the prophylactic and/or therapeutic improvement of the duration of mammalian muscle function and/or treatment of mammalian muscle disorders or diseases, comprising at least one type of xanthophylles.

In a preferred embodiment the type of xanthophyll is astaxanthin, particularly in a form esterified with fatty acids.

In a most preferred embodiment the astaxanthin in esterified form with fatty acids is algal meal of cultured Haematococcus sp.

Examples of mammalian muscle disorders or diseases include human myopaties and connective tissue diseases, as well as equine myopaties and connective tissue diseases.

In a particular embodiment of the invention, the mammalian muscle disorder is equine Exertional Rhabdomyolysis.

The medicament according to the invention may comprise a mixture of different types of xanthophylles or different forms of the same xanthophyll, such as a mixture of synthetic astaxanthin and naturally produced astaxanthin.

The medicament of the invention may comprise additional ingredients which are pharmacologically acceptable inactive or active in prophylactic and/or therapeutic use, such as flavoring agents, excipients, diluents, carriers, etc., and it may be presented in a separate unit dose or in admixture with food or feed. Examples of separate unit doses are tablets, gelatin capsules and predetermined amounts of solutions, e. g. oil solutions, or emulsions, e.g. water-in-oil or oil-in-water emulsions. Examples of food in which the preparation of the invention may be incorporated is dairy products, such as joughurt, chocolate and cereals. The daily doses of the xanthophyll in the medicament of the invention will normally be in the range of 0.01 to 1 mg per kg body weight.

The present invention also comprises the use of at least one type of xanthophylies in the preparation of a medicament for the prophylactic and/or therapeutic improvement of the duration of mammalian muscle function and/or treatment of mammalian muscle disorders or diseases. Once again, the preferred type of xanthophyll is astaxanthin, particularly in a form esterified with fatty acids, e.g. in the form of algal meal of cultured Haematococcus sp.; and in a specific embodiment the mammalian muscle disorder is equine Exertional Rhabdomyolysis.

Further, the invention comprises a method of prophylactic and/or therapeutic improvement of the duration of mammalian muscle function and/or treatment of mammalian muscle disorders or diseases, e.g. equine Exertional Rhabdomyolysis, comprising administration to said mammal of a prophylactically and/or therapeutically effective dose of a medicament according to the invention.

SHORT DESCRIPTION OF THE DRAWINGS

EXPERIMENTS

The medicament used in the experiments is the xanthophyll astaxanthin which was produced via culturing of the algae Haematococcus sp. by AstaCarotene AB, Gustavsberg, Sweden.

Astaxanthin from other sources, and other xanthophylles as well, are expected to be similarly useful for the purposes of the invention. An advantage of using astaxanthin from algae is, however, that the astaxanthin exists in a form esterified with fatty acids [Renström B. et al, 1981, Phytochem 20(11):2561–2564], which esterified astaxanthin thereby is more stable during handling and storage than free astaxanthin.

Uptake of Astaxanthin in Rat

The experiment was conducted to establish if astaxanthin in the form of algal meal was taken up by rat and to see in which organs and tissues astaxanthin is accumulated.

Performance

A medicament in the form of feed containing 100 mg astaxanthin per kg feed in the form of algal meal was prepared. Twenty-four male rats were divided into two groups; one group received feed without algal meal, and the other group received the feed containing algal meal. After three weeks 6 rats from each group were sacrificed, and the remaining rats were sacrificed after 6 weeks. At slaughter organs were excised, i. a. thigh muscle and heart, and they were freezed for later analysis of the content of carotenoids with the aid of HPLC.

Results

Figure 1:
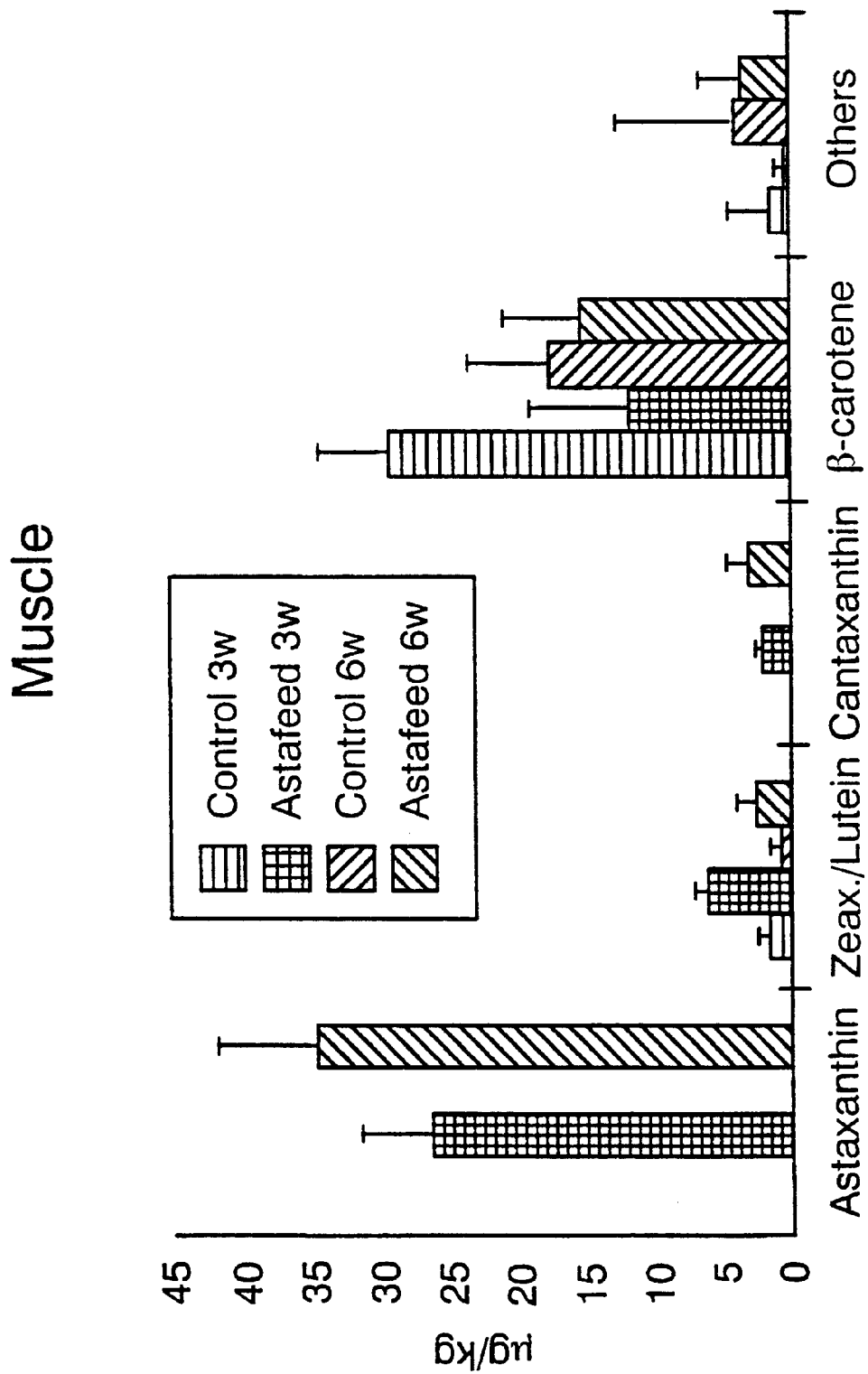
FIG. 1 is a diagram showing the up-take of different carotenoids, e.g. astaxanthin, in rat muscle.
Figure 2:
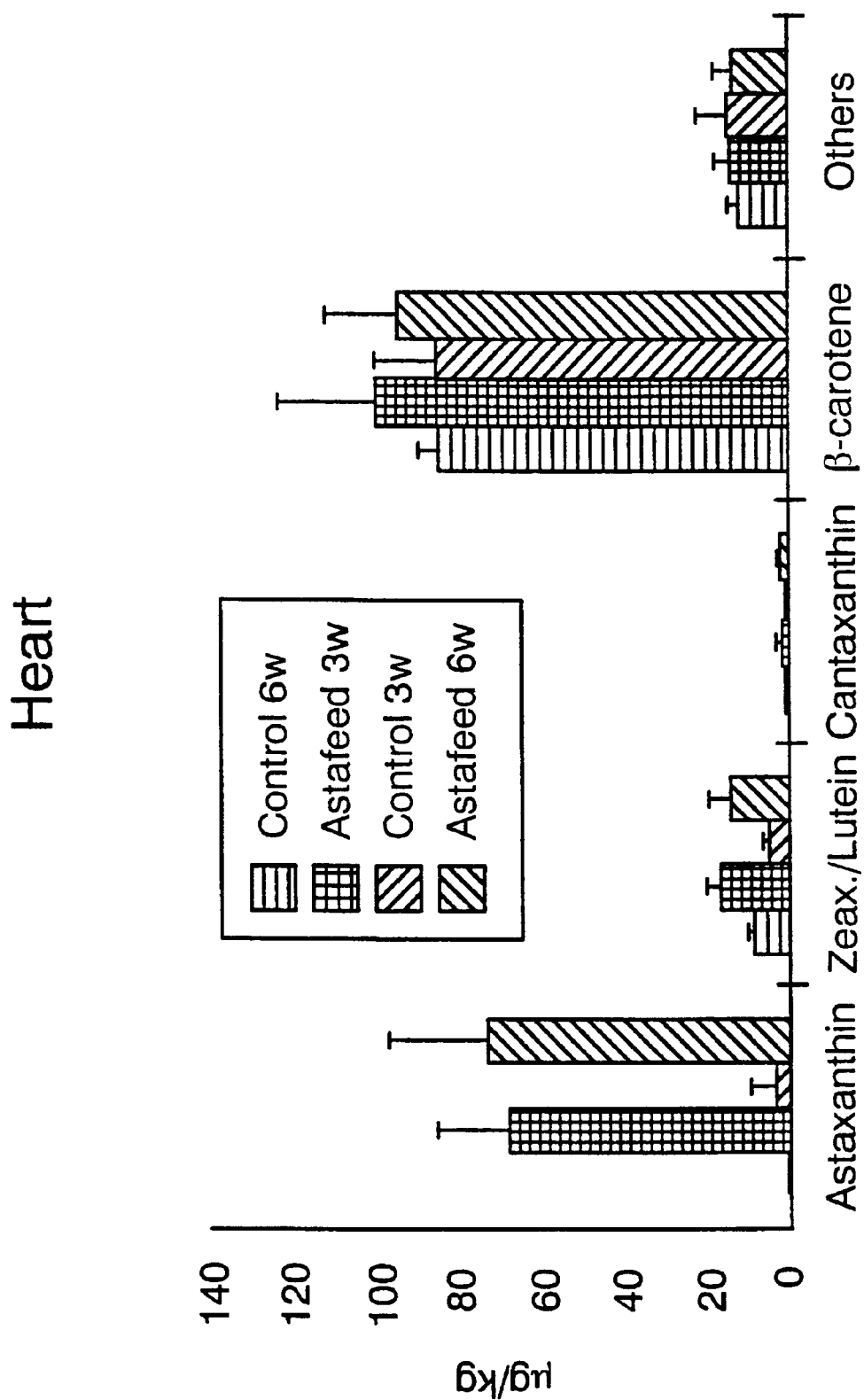
FIG. 2 is a diagram showing the up-take of different carotenoids, e.g. astaxanthin, in rat heart.

Astaxanthin could be demonstrated in both thigh muscle (see FIG. 1) and heart (see FIG. 2) of those rats that had received the feed supplemented with algal meal. In the control group, astaxanthin was not detectable.

Figure 3:
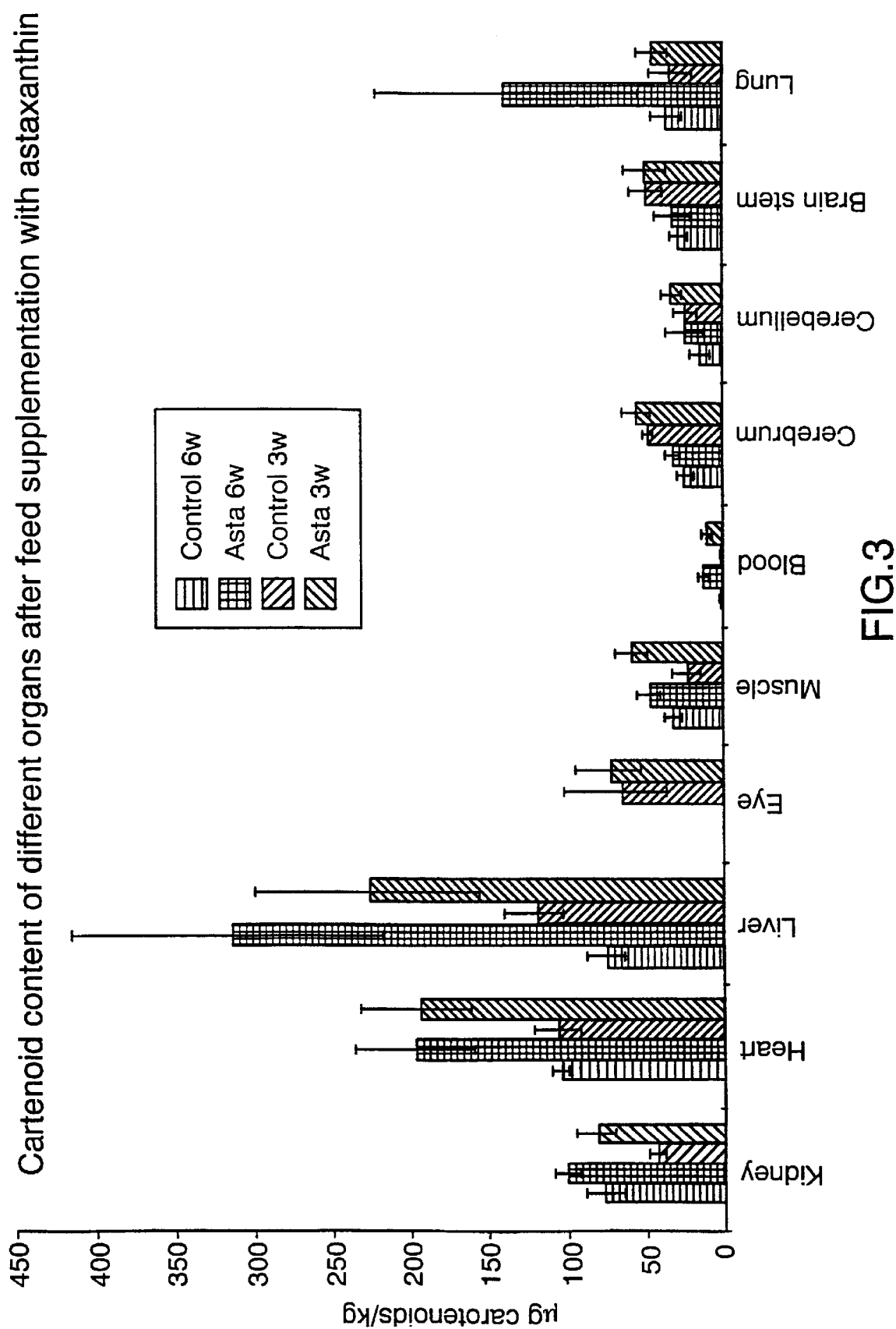
FIG. 3 is a diagram showing the carotenoid content in different rat organs after feed supplementation with astaxanthin.

Muscular tissue and particularly heart showed amongst the highest levels of astaxanthin after supplementation compared to the rest of the examined organs (see FIG. 3)

Effect of Astaxanthin in Horse

This preliminary experiment was conducted to establish if astaxanthin is taken up by horses and if supplementation with astaxanthin in the form of algal meal would improve the physical performance of trotting-horses.

Dosage

The horses received 100 mg astaxanthin per horse (approx. 500 kg) per day in the form of algal meal. The meal was supplied to the horses either sprinkled on concentrated feed or in the form of oil suspension.

Uptake

Astaxanthin could be demonstrated in muscles from horses that had received supplementation with the algal meal. The analyses were performed with the aid of HPLC on muscle biopsies. Astaxanthin could also be demonstrated in plasma samples from horses who had received the supplementation.

Effects

The most striking effect of the supplementation has been on horses suffering from muscle problems, so-called Exertional Rhabdomyolysis. In some horses this disorder appears when they are trained and raced regularly. It is not known what it is that causes the problems, but it is believed that the muscles are tightened and therefore the circulation is impaired, resulting in degradation of the muscular tissue. Today, there is no remedy for the problem except rest and increased dosage of vitamin E in the feed.

Problem-horses who have received the astaxanthin-supplementation have been free from the symptom after 2–3 weeks, and they have been able to train and race in a normal way. In cases where the supplementation has been stopped or the dosage has been less than 30 mg astaxanthin per day, the septum has reoccurred after approximately 2 weeks. The algal meal supplement has been given to a total of 8 so-called problem-horses, and they have all responded positively to the supplementation.

Effect of Astaxanthin on the Physical Performance of Humans

The experiment was conducted so that for a period of 6 months, 20 healthy volunteers received 1 capsule containing 4 mg astaxanthin in the form of algal meal each morning in association with food, and 20 healthy volunteers received 1 capsule containing placebo.

Before the experiment was started, reference values were registered for each person with regard to strength/endurance, strength/explosiveness, condition, and weight.

Performance

The strength/endurance was estimated when a person made a maximum number of knee-bending in a Smith-machine with 40 kg load under standardized conditions.

The strength/explosiveness was tested under standardized conditions in a Wingate-machine with individually adapted load and registration of maximum effect during 30 seconds. The values were related to effect/kg of body weight.

The condition was tested by a step test with 17 kg load and bench height of 32 cm until steady state pulse was reached. (I.e. the pulse did not differ more than three strokes from the measurement of the previous minute).

The weight difference between before and after the experiment was checked with a digital scale.

Results

No significant difference was established between the astaxanthin group and the placebo group in any of the tested parameters due to the small number of test persons.

With regard to condition ($VO_2$ max./kg, minute) there was no significant difference between the groups; a reduction of 1.75% for the astaxanthin group and 1.37% for the placebo group.

A reduction was also seen for both groups in the (strength/explosiveness) Wingate test (W/7 kg); −4.13% for the astaxanthin group and −5.81% for the placebo group.

Both groups gained weight; 1.0% for the astaxanthin group and 2.1% for the placebo group. However, the individual differences were quite large, and no tendency could be established.

However, there was a clear difference between the groups in the strength/endurance test; 61.74% for the astaxanthin group and 23.78% for the placebo group.

In summary, the positive performance effect that was attributed to astaxanthin by individual athletes does not seem to be related to an increased condition or explosive strength but to strength/endurance according to this experiment.

What is claimed is:

1. A method of prophylactic and/or therapeutic improvement of the duration of muscle function and/or treatment of muscle disorders or diseases in a mammal in need thereof, comprising administration to said mammal of a prophylactically and/or therapeutically effective dose of a medicament comprising astaxanthin.

2. The method according to claim 1, wherein the astaxanthin is in a form esterified with fatty acids.

3. The method according to claim 2, wherein the astaxanthin in esterified form is algal meal of cultured Haematococcus sp.

4. The method according to claim 1, wherein said mammalian muscle disorder is equine Exertional Rhabdomyolysis.

5. The method according to claim 2, wherein said mammalian muscle disorder is equine Exertional Rhabdomyolysis.

6. The method according to claim 3, wherein said mammalian muscle disorder is equine Exertional Rhabdomyolysis.

7. A method for therapeutic improvement of the duration of muscle function, the treatment of muscle disorders or diseases in a mammal in need thereof comprising administering to said mammal a therapeutically effective dose of a medicament comprising astaxanthin.

8. The method according to claim 7, wherein the astaxanthin is in a form esterified with fatty acids.

9. The method according to claim 7, wherein the astaxanthin in esterified form is algal meal of cultured Haematococcus sp.

10. The method according to claim 7, wherein said mammalian muscle disorder is equine Exertional Rhabdomyolysis.

* * * * *